US009421332B2

(12) United States Patent
Valk et al.

(10) Patent No.: US 9,421,332 B2
(45) Date of Patent: Aug. 23, 2016

(54) BALANCED PHYSIOLOGICAL MONITORING AND TREATMENT SYSTEM

(71) Applicants: Jeffrey W. Valk, Boston, MA (US); Timothy W. Valk, Orlando, FL (US)

(72) Inventors: Jeffrey W. Valk, Boston, MA (US); Timothy W. Valk, Orlando, FL (US)

(73) Assignee: ADMETSYS CORPORATION, Boston, MA (US)

( * ) Notice: Subject to any disclaimer, the term of this patent is extended or adjusted under 35 U.S.C. 154(b) by 0 days.

(21) Appl. No.: 14/596,916

(22) Filed: Jan. 14, 2015

(65) Prior Publication Data
US 2015/0157795 A1 Jun. 11, 2015

Related U.S. Application Data

(63) Continuation of application No. 11/816,821, filed as application No. PCT/US2006/006229 on Feb. 22, 2006, now Pat. No. 8,956,291.

(60) Provisional application No. 60/656,575, filed on Feb. 22, 2005.

(51) Int. Cl.
*A61B 5/00* (2006.01)
*A61M 5/172* (2006.01)
(Continued)

(52) U.S. Cl.
CPC ............ *A61M 5/1723* (2013.01); *A61B 5/021* (2013.01); *A61B 5/024* (2013.01); *A61B 5/026* (2013.01);
(Continued)

(58) Field of Classification Search
CPC .. G06F 19/34; G06F 19/706; A61M 5/16827; A61B 5/021; A61B 5/024; A61B 5/04; A61B 5/14542; A61B 5/4839
See application file for complete search history.

(56) References Cited

U.S. PATENT DOCUMENTS 4,055,175 A 10/1977 Clemens et al.
4,526,569 A 7/1985 Bernardi
(Continued)

FOREIGN PATENT DOCUMENTS

DE 10352456 A1 7/2005
WO WO 98/34657 A2 8/1998
(Continued)

OTHER PUBLICATIONS

Extended European Search Report, issued by the European Patent Office, regarding corresponding patent application Serial No. 13159283.4, dated Jun. 4, 2013, 7 pages.
(Continued)

Primary Examiner — Christian Jang
(74) Attorney, Agent, or Firm — Barbara A. Wrigley; Fox Rothschild LLP

(57) ABSTRACT

A system and method for providing balanced, automated regulation of a patient's physiological condition by monitoring at least one physiological parameter and, optionally, monitoring and controlling additional physiological parameters, is disclosed. The system includes a physiological parameter monitor, an intelligent control device and a multi-channel delivery device for providing controlled intravenous delivery of at least two medications that affect the physiological condition being controlled. Control logic in the intelligent control device is derived by an algorithm based on model predictive control. The control logic includes mathematically modeled systems, empirical data systems or a combination thereof. The system of the present invention is optionally included in a networked system to provide centralized data storage and archival of system information as well as data export and query capabilities that can be used for patient file management, health care facility management and medical research.

22 Claims, 7 Drawing Sheets

(51) Int. Cl.

| | | |
|---|---|---|
| *A61B 5/021* | (2006.01) | |
| *A61B 5/024* | (2006.01) | |
| *A61B 5/026* | (2006.01) | |
| *A61B 5/145* | (2006.01) | |
| *A61M 5/168* | (2006.01) | |
| *A61B 5/02* | (2006.01) | |
| *A61B 5/029* | (2006.01) | |
| *G06F 19/00* | (2011.01) | |

(52) U.S. Cl.
CPC ......... *A61B 5/02007* (2013.01); *A61B 5/14532* (2013.01); *A61B 5/4839* (2013.01); *A61M 5/16827* (2013.01); *A61B 5/029* (2013.01); *A61B 5/145* (2013.01); *A61M 2230/201* (2013.01); *G06F 19/3468* (2013.01)

(56) References Cited

U.S. PATENT DOCUMENTS

| | | |
|---|---|---|
| 4,538,616 A | 9/1985 | Rogoff |
| 4,619,261 A | 10/1986 | Guerriero |
| 4,633,878 A | 1/1987 | Bombardieri |
| 5,109,866 A | 5/1992 | Guegan et al. |
| 5,474,552 A | 12/1995 | Palti |
| 5,630,706 A | 5/1997 | Yang |
| 5,984,893 A | 11/1999 | Ward |
| 6,017,318 A | 1/2000 | Gauthier et al. |
| 6,017,494 A | 1/2000 | Ashihara et al. |
| 6,056,734 A | 5/2000 | Jacobsen et al. |
| 6,063,028 A | 5/2000 | Luciano |
| 6,233,539 B1 | 5/2001 | Brown |
| 6,544,212 B2 | 4/2003 | Galley et al. |
| 6,572,542 B1 | 6/2003 | Houben et al. |
| 6,740,072 B2 | 5/2004 | Starkweather et al. |
| 6,743,202 B2 | 6/2004 | Hirschman et al. |
| 6,958,053 B1 | 10/2005 | Reilly |
| 6,966,880 B2 | 11/2005 | Boecker et al. |
| 6,980,958 B1 | 12/2005 | Surwit et al. |
| 7,029,456 B2 | 4/2006 | Ware et al. |
| 7,204,823 B2 | 4/2007 | Estes et al. |
| 7,367,942 B2 | 5/2008 | Grage et al. |
| 7,481,818 B2 | 1/2009 | Allen et al. |
| 7,491,187 B2 | 2/2009 | Van Den Berghe et al. |
| 7,509,156 B2 | 3/2009 | Flanders |
| 7,604,619 B2 | 10/2009 | Eich et al. |
| 7,608,042 B2 | 10/2009 | Goldberger et al. |
| 7,785,258 B2 | 8/2010 | Braig et al. |
| 7,811,246 B2 | 10/2010 | Koops |
| 7,811,279 B2 | 10/2010 | John |
| 7,859,473 B2 | 12/2010 | Gibson |
| 7,914,499 B2 | 3/2011 | Gonnelli et al. |
| 8,121,857 B2 | 2/2012 | Galasso et al. |
| 8,209,060 B2 | 6/2012 | Ledford |
| 8,226,556 B2 | 7/2012 | Hayes et al. |
| 8,273,052 B2 | 9/2012 | Damiano et al. |
| 8,303,533 B2 | 11/2012 | Regittnig et al. |
| 8,343,092 B2 | 1/2013 | Rush et al. |
| 8,377,031 B2 | 2/2013 | Hayter et al. |
| 8,388,598 B2 | 3/2013 | Steinkogler |
| 8,425,417 B2 | 4/2013 | Leach et al. |
| 8,449,524 B2 | 5/2013 | Braig et al. |
| 2001/0044584 A1 | 11/2001 | Kensey |
| 2002/0099273 A1 | 7/2002 | Bocionek et al. |
| 2003/0031591 A1 | 2/2003 | Whitson et al. |
| 2003/0031595 A1 | 2/2003 | Kirchhevel et al. |
| 2003/0208113 A1 | 11/2003 | Mault et al. |
| 2004/0147969 A1 | 7/2004 | Mann et al. |
| 2005/0015001 A1 | 1/2005 | Lec et al. |
| 2005/0234486 A1 | 10/2005 | Allen et al. |
| 2006/0224141 A1 | 10/2006 | Rush et al. |
| 2007/0015972 A1 | 1/2007 | Wang et al. |
| 2007/0060803 A1 | 3/2007 | Liljeryd et al. |
| 2007/0088271 A1 | 4/2007 | Richards |
| 2007/0149466 A1 | 6/2007 | Milburn et al. |
| 2007/0225675 A1 | 9/2007 | Robinson et al. |
| 2008/0021294 A1 | 1/2008 | Levin et al. |
| 2008/0077048 A1 | 3/2008 | Escutia |
| 2009/0069743 A1 | 3/2009 | Krishnamoorthy et al. |
| 2009/0076383 A1 | 3/2009 | Toews et al. |
| 2009/0227989 A1 | 9/2009 | Burke et al. |
| 2010/0057057 A1 | 3/2010 | Hayter et al. |
| 2010/0137828 A1 | 6/2010 | Michard et al. |
| 2010/0145173 A1 | 6/2010 | Alferness et al. |
| 2010/0145303 A1 | 6/2010 | Yodfat et al. |
| 2010/0174228 A1 | 7/2010 | Buckingham et al. |
| 2010/0217238 A1 | 8/2010 | DeJournett |
| 2010/0249561 A1 | 9/2010 | Patek et al. |
| 2010/0262117 A1 | 10/2010 | Magni et al. |
| 2010/0271213 A1 | 10/2010 | Krainz et al. |
| 2010/0324382 A1 | 12/2010 | Cantwell et al. |
| 2011/0021978 A1 | 1/2011 | Martin et al. |
| 2011/0184266 A1 | 7/2011 | Levin |
| 2011/0282320 A1 | 11/2011 | Steil et al. |
| 2012/0071819 A1 | 3/2012 | Bruggemann et al. |
| 2012/0123234 A1 | 5/2012 | Atlas et al. |
| 2012/0179135 A1 | 7/2012 | Rinehart et al. |
| 2012/0195182 A1 | 8/2012 | Pommereau et al. |
| 2012/0275957 A1 | 11/2012 | Creaven et al. |
| 2012/0330228 A1 | 12/2012 | Day et al. |
| 2013/0165900 A1 | 6/2013 | Braig et al. |
| 2013/0190674 A1 | 7/2013 | Case et al. |

FOREIGN PATENT DOCUMENTS

| | | |
|---|---|---|
| WO | WO 01/50950 A2 | 7/2001 |
| WO | WO 2004/112603 A1 | 12/2004 |
| WO | WO 2005/072792 A1 | 8/2005 |
| WO | WO 2006/091650 A2 | 8/2006 |
| WO | WO 2007/051139 A2 | 5/2007 |
| WO | WO 2007/116226 A2 | 10/2007 |
| WO | WO 2008/081444 A2 | 7/2008 |
| WO | WO 2008/113772 A1 | 9/2008 |
| WO | WO 2013/032965 A1 | 3/2013 |

OTHER PUBLICATIONS

Extended European Search Report, issued by the European Patent Office, regarding corresponding patent application Serial No. 06735761, dated Aug. 11, 2009; 10 pages.

International Search Report and Written Opinion, issued by the U.S. Receiving Office of United States Patent and Trademark Office, regarding corresponding patent application Serial No. PCT/US2006/006229, dated Sep. 13, 2006; 6 pages.

BALANCED PHYSIOLOGICAL MONITORING AND TREATMENT SYSTEM

CROSS REFERENCE TO RELATED APPLICATIONS

This application is a continuation patent application of U.S. patent application Ser. No. 11/816,821, filed on Aug. 21, 2007, which is a national stage patent application of International patent application Serial No.: PCT/US2006/006229, filed on Feb. 22, 2006, which claims the benefit of provisional patent application Ser. No. 60/656,575, filed on Feb. 22, 2005, the entireties of which are incorporated by reference herein.

BACKGROUND OF THE INVENTION

1. Field of the Invention

The present invention relates to a system for monitoring and treating at least one physiological condition of a patient. More particularly, the present invention relates to a system and method for providing a balanced, regulated treatment of the physiological condition based on monitoring and controlling one or more predetermined physiological parameters.

2. Discussion of Related Art

Healthcare professionals in intensive care facilities are often faced with treating patients for one type of physiological condition while monitoring at least one of a host of physiological parameters. It is often necessary to deliver various medications to patients in order to control these physiological parameters. Monitoring and controlling multiple physiological parameters for a plurality of patients requires a great deal of time and resources from healthcare professionals. With ever increasing shortages in healthcare staff, workloads have been shown to be directly proportional to an increase in the occurrence of errors in medication delivery. Errors in medication delivery occur more frequently than commonly known and many of the errors are life threatening. In addition, these errors often go undiscovered and/or unreported.

There are several physiological conditions that are monitored in an intensive care setting, namely hypoglycemia, blood clotting, and the overall physiological stability of the patient. Typically, however, healthcare providers will measure only one physiological parameter, such as glucose level, prothrombin time, blood flow, hemoglobin level, heart rate, blood pressure, arterial oxygen concentration and other cardiac output, to treat the specific physiological condition under examination. Based on this measurement or a series of these measurements, the provider delivers medication to the patient in order to stabilize the physiological parameter and thus treat the physiological condition.

The control of glucose levels in seriously ill patients has proven to be a significant problem. Hyperglycemia is a frequent consequence of severe illness, occurring in both diabetic and non-diabetic patients, due to altered metabolic and hormonal systems, impaired gastrointestinal motility, altered cardiac function, increased catecholamine production, altered hepatic gluconeogenesis, relative insulin resistance and increased corticosteroid levels. Symptoms associated with elevated levels of blood glucose include dehydration, weakness, greater risk of poor healing and infection, frequent urination, and thirst. Infusion of insulin has proven an effective method for treating hyperglycemia. However, insulin infusion without proper glucose level monitoring can lead to problems with hypoglycemia.

Hypoglycemia in both diabetic and non-diabetic patients is one physiological condition that is monitored in an intensive care and/or other acute medical setting. Hypoglycemia is a common problem with severely ill patients and is defined as the fall of blood and tissue glucose levels to below 72 mg/dl. Symptoms associated with decreased levels of blood and tissue glucose levels are weakness, sweating, loss of concentration, shakiness, nervousness, change in vision and if untreated, loss of consciousness, possible seizures and neurological sequelae such as paralysis and death. Treatment in the case of both hyperglycemia and hypoglycemia involves monitoring and controlling the patient's glucose level.

Medical studies have established a direct correlation between morbidity and mortality in intensive care patients and the degree of glucose control. The use of intravenous insulin has vastly increased the efficacy of glucose control and has proven to be superior to conventional insulin treatment in reducing morbidity and mortality among patients in intensive care.

Data provided in medical studies indicates that hypoglycemia occurs in 3.8%-4% of all patients when glucose is measured every 2 hours. In other words, the average patient has a hypoglycemic episode every 2 to 4 days. The mean time that patients spent in the intensive care unit in these studies was between 2.5 and 10 days. Thus, theoretically, the average patient would have at least 1 and possibly up to 5 episodes of hypoglycemia during their intensive care unit stay. To reduce the risk of hypoglycemia, the burden is on nurses to monitor patient glucose levels every 1 to 1.5 hours. In addition, nurses must implement increasingly complex procedures to monitor and control patients' glucose levels. This level of attention by healthcare professionals is not practical for busy hospital intensive care units. Furthermore, as a result of increases in medical malpractice claims, stricter control regimens have been imposed on hospital staffs. These control regimens are often complex and increase the already heavy burden on health care professionals.

Systems and methods for monitoring and controlling glucose levels in intensive care units are known. One such system requires manual adjustment of the intravenous insulin using a single normogram or algorithmic sequence, where various adjustments are manually made over time. This system involves periodic measurements (typically hourly) of the patient's blood glucose level taken by nursing staff. The nursing staff must then obtain orders from a doctor to adjust the amount of insulin being delivered to the patient in an effort to maintain the patient's blood glucose level within a desired range. This method is time consuming, costly and prone to error.

Also known are systems and methods for monitoring and controlling blood glucose levels with an algorithm having a modifier to adjust the patient's insulin rate based on the level of the immediately preceding glucose measurement. If the glucose level declines too quickly, a negative modifier slows the intravenous insulin delivery rate. Alternatively, if the glucose level increases too quickly, the negative modifier increases the intravenous insulin delivery rate. This system is complex to run because multiple glucose level measurements are necessary to determine the rate of the intravenous insulin delivery. Thus, healthcare professionals spend additional time and resources on using this type of system.

Further, neither of the aforementioned systems includes a counterbalancing glucose infusion algorithm. The use of intravenously delivered insulin alone is unbalanced in that no counteracting glucose solution is activated when measurements indicate that glucose is declining. In systems currently available, a patient on intravenous insulin is given a bolus, or a concentrated infusion of glucose to counteract hypoglycemia, only after his or her glucose level reaches a particular level. While the insulin rate may be reduced or stopped altogether at low glucose levels, the effects of insulin at the tissue level persist and hypoglycemia may nevertheless develop. Moreover, insulin infusion rates cover a wide distribution of glucose readings. For example, minimum rates of 0.5-1.0 units of insulin per hour may start at glucose levels from about 80 to about 120 mg/dl, while maximum rates of insulin delivery may start at glucose levels as low as about 10 units per hour to those which have no apparent upper endpoint. Because of these variables, it is difficult for healthcare professionals to determine the precise time to provide counterbalancing glucose infusions. Accordingly, there exists a need for a computerized monitoring and control system that assists healthcare professionals in monitoring hypoglycemia by measuring glucose levels, projecting future values and setting the infusion rate of glucose and insulin based on these values.

It would also be useful to monitor and control blood clotting in seriously ill patients. Blood clots (fibrin clots) result from coagulation of the blood. A blood clot that forms in a vessel or within the heart and remains there is called a thrombus. A thrombus that travels from the vessel or heart chamber where it formed to another location in the body is called an embolus, and the disorder, an embolism. For example, an embolus that occurs in the lungs is called a pulmonary embolism. Thrombi and emboli can firmly attach to a blood vessel and partially or completely block the flow of blood in that vessel. This blockage deprives the tissues in that location of normal blood flow and oxygen. Thus, it is important to monitor and control blood clotting in seriously ill patients to reduce the risk of stroke and other life threatening complications.

However, monitoring and controlling blood clotting is inherently complicated. Patients who receive excessive amounts of an anticoagulant can suffer from unusually heavy bleeding episodes. This can be particularly dangerous for intensive care patients who have sustained surgical wounds, the elderly who are especially sensitive to anticoagulants, heart patients, and children. Thus, healthcare professionals typically monitor patients for signs of excessive bleeding in order to provide the correct doses of either a coagulant or an anticoagulant. Presently available methods include observation and manual delivery of these medications. Accordingly, there also exists a need for a computerized monitoring and control system that assists healthcare professionals in monitoring blood coagulation by direct or indirect measurement of coagulation status, including intrinsic or extrinsic clotting factors, projecting future values and setting the infusion rate of a blood coagulant and anticoagulant based on these values.

As yet another example, health care professionals also monitor the overall physiological stability of intensive care unit patients by monitoring physiological parameters such as blood flow, heart rate, blood pressure, hemoglobin levels, cardiac output, arterial oxygen concentration and other factors. All of these physiological parameters are affected by vasodilators and vasoconstrictors.

Electron beam CT scanners for tracking blood flow by acquiring images of pulmonary anatomy and function are known. By using an appropriate blood flow model, regional parenchymal time-intensity curves, sampled from dynamic CT scans of a bolus contrast injection, can be used to calculate regional blood flow, regional air, blood and tissue percentages, in addition to regional contrast mean transit times and arrival times. Computerized systems are used to convert data taken from the scans into blood flow calculations, color coded images, and the like.

Thermographic cameras are also known and are used to record infrared radiation, or heat, rather than visible light. In this manner, a thermographic camera identifies differences in blood flow because warmer areas record greater blood flows. Ultrasound monitoring, also known, measures the speed with which blood flows through blood vessels. This method can detect blood vessel constriction as well as blood flow abnormalities.

While all of these systems are useful to monitor patient blood flow, they do not provide a means for controlling the blood flow of a patient nor do they provide an effective, easy way of combining data related to other parameters such as blood pressure, heart rate, hemoglobin level, arterial oxygen concentration and cardiac output to monitor overall patient stability.

Vasodilation is one parameter used to gauge overall physiological stability of a patient. It is well known that nitric oxide is a naturally occurring vasodilator present in the vascular endothelium of body tissue. Synthesis of nitric oxide is modulated by shear stress in the vessel walls. This helps match vessel caliber to blood flow. At a cellular level it works by converting guanylyl cyclase to cyclic glycomacropeptide (GMP) which in turn relaxes vascular smooth muscle. The use of inhaled nitric oxide is widely known as a means to reduce pulmonary vascular resistance and improve the ventilation/perfusion relationship in patients with acute hypoxic respiratory failure, acute lung injury or right ventricular overload.

One technique that is used to boost nitric oxide production in severely ill patients on ventilators involves manually adding a continuous stream of nitrogen/nitric oxide mixture into an inspiratory limb of a ventilator, usually as close to the ventilator as possible to give time for the nitric oxide to mix before it reaches the patient. A monitor that analyzes nitric oxide and nitrogen dioxide is placed at the distal end of the inspiratory limb. The flow of nitrogen/nitric oxide is controlled by a needle valve and rotameter and manually adjusted to give the required inspired concentration.

Another technique commonly used to boost nitric oxide production involves administering L-arginine to ICU patients. One such technique includes ingestion of orally administered L-arginine. Administration of enteral L-arginine is limited in that noticeable increases of nitric oxide production in patients generally occur 2 to 4 hours after ingesting the L-arginine. Another technique involves parenteral administration of L-arginine, including intravenous injections. Other techniques for boosting nitric oxide levels in patients include pulsatile or continuous infusion of insulin or phosphodiesterase.

Vasoconstriction is another parameter used to gauge the overall physiological stability of a patient. Vasoconstriction is achieved via intravenously administered medications, such as endothelin, endothelin like compounds, sympathomimetics and vasopressin like compounds. The use of such pulmonary vasoconstrictors increases the efficacy of nitric oxide and can be instrumental in providing a required balance between vasoconstriction and vasodilatation for physiologically stabilizing a patient. However, heightened levels of vasoconstrictors, particularly endothelin, can lead to pulmonary artery hypertension and heart failure.

Because both of the foregoing techniques involve the manual introduction of medication into patients, they are inherently prone to error. Accordingly, there exists a need for computerized monitoring and control system that assists healthcare professionals in monitoring blood flow by measuring and controlling vasodilatation and vasoconstriction, projecting future vales of these parameters and setting the infusion rate of medications to treat these parameters.

Based on the foregoing examples and in light of increasing shortages in intensive care personnel, there exists an acute need for a balanced physiological monitoring and control system that uses an intelligent control device and a multi-channel delivery manifold for controlled delivery of a plurality of medications that impact a monitored physiological parameter in order to stabilize and balance a physiological condition in a patient.

SUMMARY OF THE INVENTION

It is an object of the present invention to provide a system and method for balancing a physiological condition of a patient. It is a further object of the present invention to provide a system including a physiological parameter monitor, an intelligent control device, and a multi-channel delivery manifold for adaptively stabilizing and balancing a monitored physiological parameter. It is still a further object of the present invention to provide a system which includes a physiological parameter monitor, an intelligent control device, and a multi-channel delivery manifold which controls the infusion rate of one or a plurality of medications into the patient to stabilize and balance the patient's physiological parameters and thus the physiological condition. It is still a further object of the present invention to provide a system for short term, intensive treatment for critical care patients which adaptively stabilizes and balances a plurality of physiological parameters in the patient and which provides for multi-channel infusion of a plurality of medications that impact the physiological parameters and in turn the physiological condition of the patient. It is still a further object of the present invention to provide a system for balanced automated regulation of a physiological condition in a patient, wherein the system is adapted for integration with a network to provide for remote monitoring, management and control of multiple infusion devices, centralized data storage and archival of information, patient file management, hospital/clinic unit management and medical research.

These and other objects and advantages of the present invention are accomplished by the system and method for monitoring and controlling a physiological condition of a patient in accordance with the present invention. The system includes at least one physiological parameter monitor adapted to monitor a physiological parameter of a patient, a control device operably connected to the physiological parameter monitor, the control device having control logic that is capable of monitoring, receiving and storing physiological parameter data from the physiological parameter monitor and translating the physiological parameter data into an output control signal containing information regarding administration of at least two medications, and a delivery manifold operably connected to the control device, the delivery manifold capable of receiving the output control signal from the control device, where the delivery manifold infuses at least two medications into the patient based on the information contained in the output control signal.

The invention will be further described with reference to the following detailed description taken in conjunction with the drawings.

DETAILED DESCRIPTION

Figure 1:
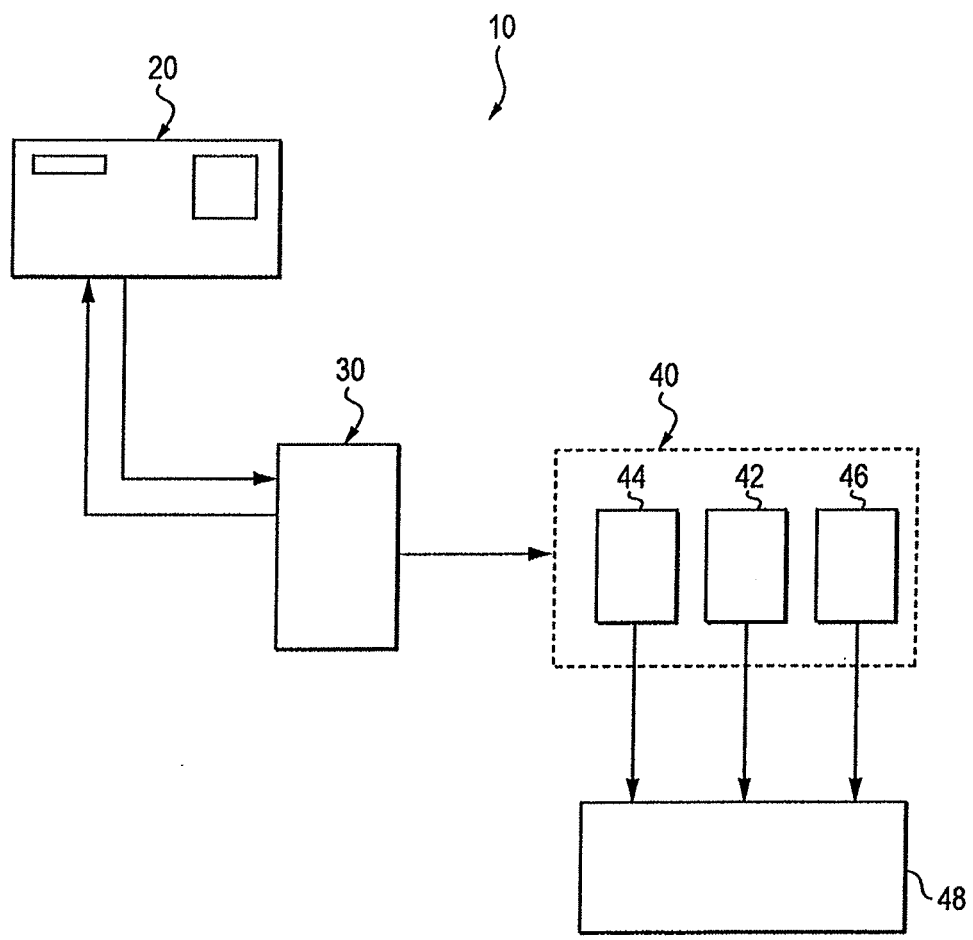
FIG. 1 is a schematic diagram of the system of the present invention illustrating the principal components thereof.

Referring to FIG. 1, a system for providing balanced, automated regulation of a physiological condition in a patient is generally indicated as 10. System 10 includes a physiological monitor 20, an intelligent electronic controller unit 30 and a multi-channel delivery mechanism 40 which may include multiple single channel delivery manifolds, one or more multiple channel delivery manifolds, or a combination of single and multiple channel delivery manifolds.

In one embodiment, the multi-channel delivery mechanism 40 includes two pumps, a first pump 42 and a second pump 44 for delivering medications to a patient. In an alternate embodiment, system 10 includes a third pump 46 for delivery of a third medication to a patient 48. In another alternate embodiment, system 10 includes four or more pumps for delivery of four or more medications to a patient. In the foregoing embodiments, the use of two, three, four or more pumps 46 allows for the concurrent monitoring and control of several physiological parameters and conditions.

Those skilled in the art will appreciate that pumps 42, 44, 46 may be selected from a wide variety of infusion pumps commonly used in the medical industry such as continuous and/or intermittent, the selection of which will vary depending on criteria such as desired flow rates and/or delivery of large or small volumes. Infusion pumps can administer fluids in ways that would be impracticably expensive or unreliable if performed manually by nursing staff. For example, they can administer as little as 0.1 mL per hour injections (too small for a drip), injections every minute, injections with repeated boluses, up to maximum number per hour, or fluids whose volumes vary by the time of day.

In one embodiment of the present invention, the outputs of pumps 42, 44, 46 are controlled by providing control valves on the feed lines to the pumps 42, 44, 46. In this embodiment, the control valves are provided with a signal related to the desired volume of each medication to be delivered to the patient. In another embodiment, pumps 42, 44, 46 are run with variable speed drives such that pump outputs are controlled by varying the speed of the drive as it relates to predetermined volume per rotation calculations for each medication being pumped. This data is stored in controller 30.

Multi-channel delivery mechanism 40 provides controlled delivery of a first medication and a second medication and optionally, three or more medications to the patient 48 as determined by controller 30. More particularly, controller 30 accepts input from a single device or a range of devices which provides data point information about a primary physiological condition and, optionally, data point information about additional physiological conditions. Controller 30 is provided with adaptive logic for gradual, optimized, stabilization of the primary physiological condition and, optionally, the additional physiological conditions. Controller 30 includes an output to multi-channel delivery mechanism 40 to thereby control the rate of flow of the first, the second and optionally the third medications to the patient 48 to maintain the patient's primary and secondary physiological conditions within a defined range.

Those skilled in the art will appreciate that the system in accordance with the present invention may include stationary systems used in intensive care units or emergency rooms in hospitals, or may comprise portable units for use by emergency medical technicians in ambulances, at the scene of accidents, and when responding to other emergency situations. Those skilled in the art will also appreciate that the system in accordance with the present invention may alternately include a miniature chip as the controller, where the chip can be operably connected to a means for encapsulating the medications being administered such that the encapsulated medications can be implanted in the patient's body and released on-demand based on an output signal from the controller.

Figure 2:
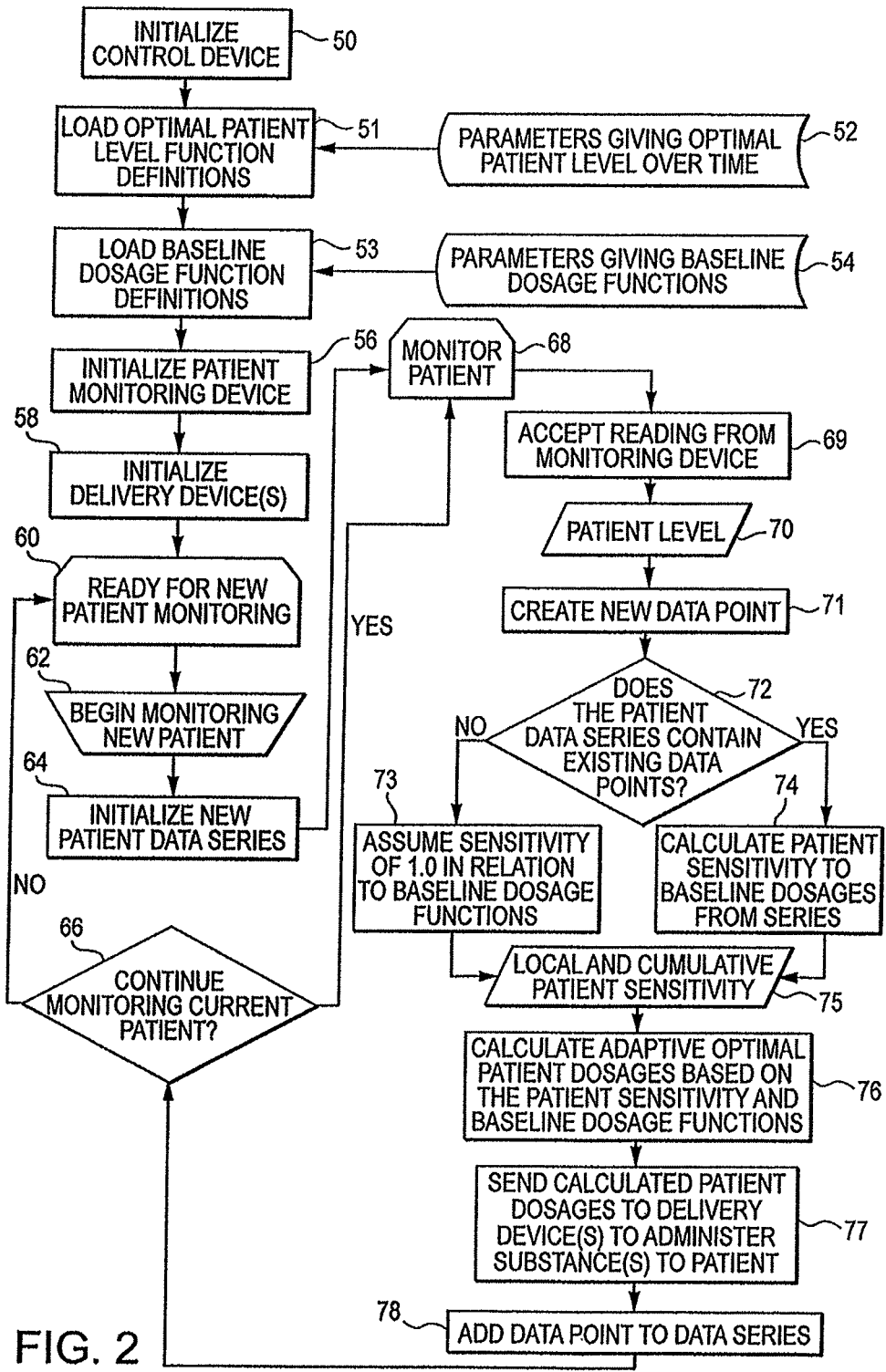
FIG. 2 is a flowchart illustrating one method of using the system of the present invention.

As illustrated in the flowchart depicted in FIG. 2, one method for monitoring and stabilizing a physiological condition in accordance with the present invention includes initializing a control device 50; loading definitions for optimal patient level 51 where parameters are defined for optimal patient level over time 52; loading definitions for a baseline dosage function 53 where parameters are defined for baseline dosages over time 54; initializing a patient monitoring device 56; initializing a delivery device 58; determining if the system is ready to monitor a new patient 60; monitoring a new patient 62; initializing a new patient data series 64; and continuously monitoring the patient 66. FIG. 2 also depicts a method for monitoring the patient 68 including accepting a reading from a monitoring device 69; determining the level of the physiological parameter 70 being monitored; creating a new data point in the data series 71; determining whether the patient data series contains existing data points 72; calculating patient sensitivity to baseline dosages if there are existing data points 74 or assuming a sensitivity of 1.0 in relation to the baseline dosage functions 73; determining local and cumulative patient sensitivity 75; calculating adaptive optimal patient dosages based on the patient sensitivity and baseline dosage functions 76; sending the calculated patient dosages to the delivery devices to administer medications to patients 77; and adding a data point to the data series 78 in order to continue to provide cumulative patient sensitivity to the medications being administered.

Figure 3:
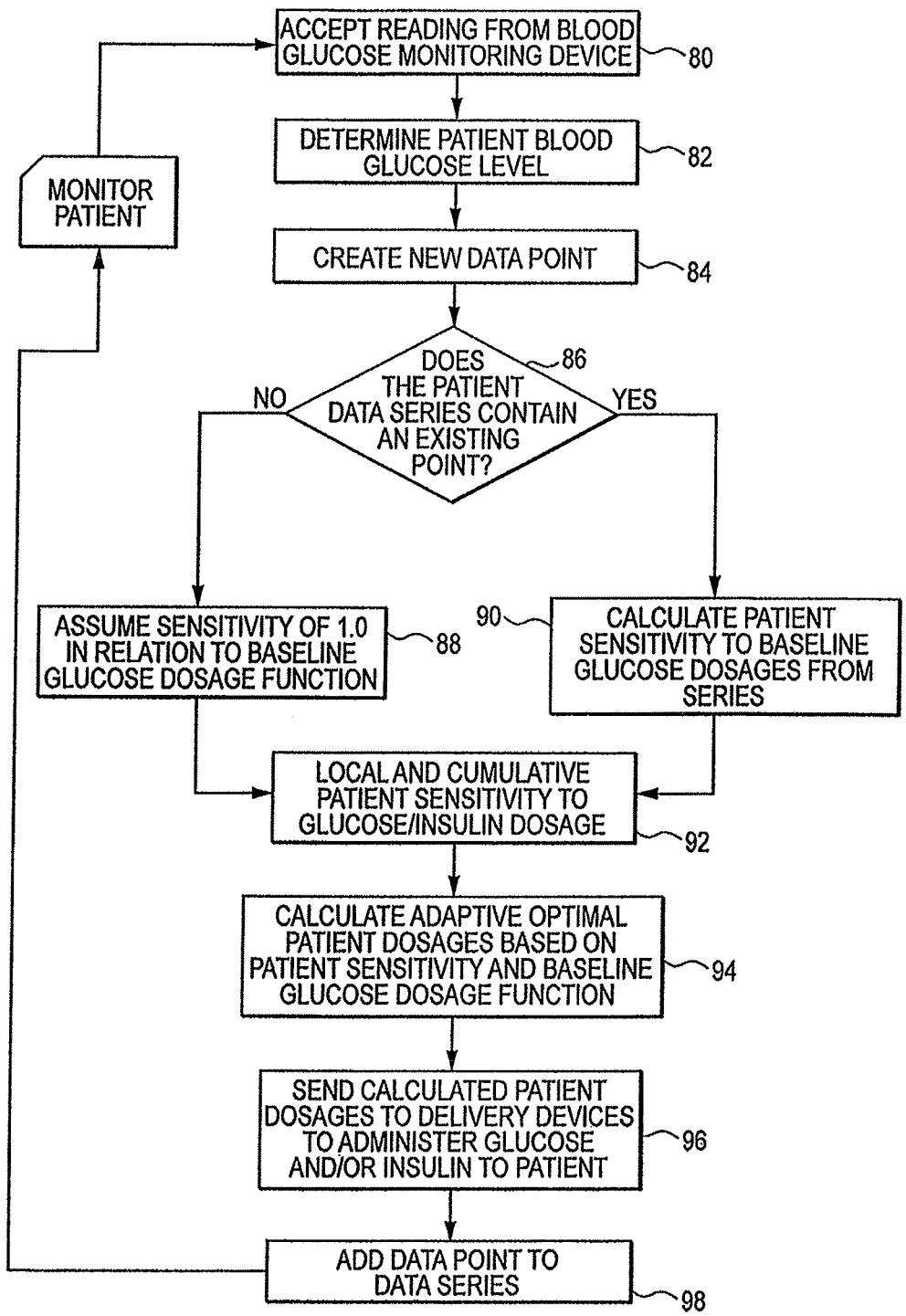
FIG. 3 is a flowchart illustrating one method of monitoring and stabilizing a physiological condition in accordance with the system of the present invention.
Figure 4:
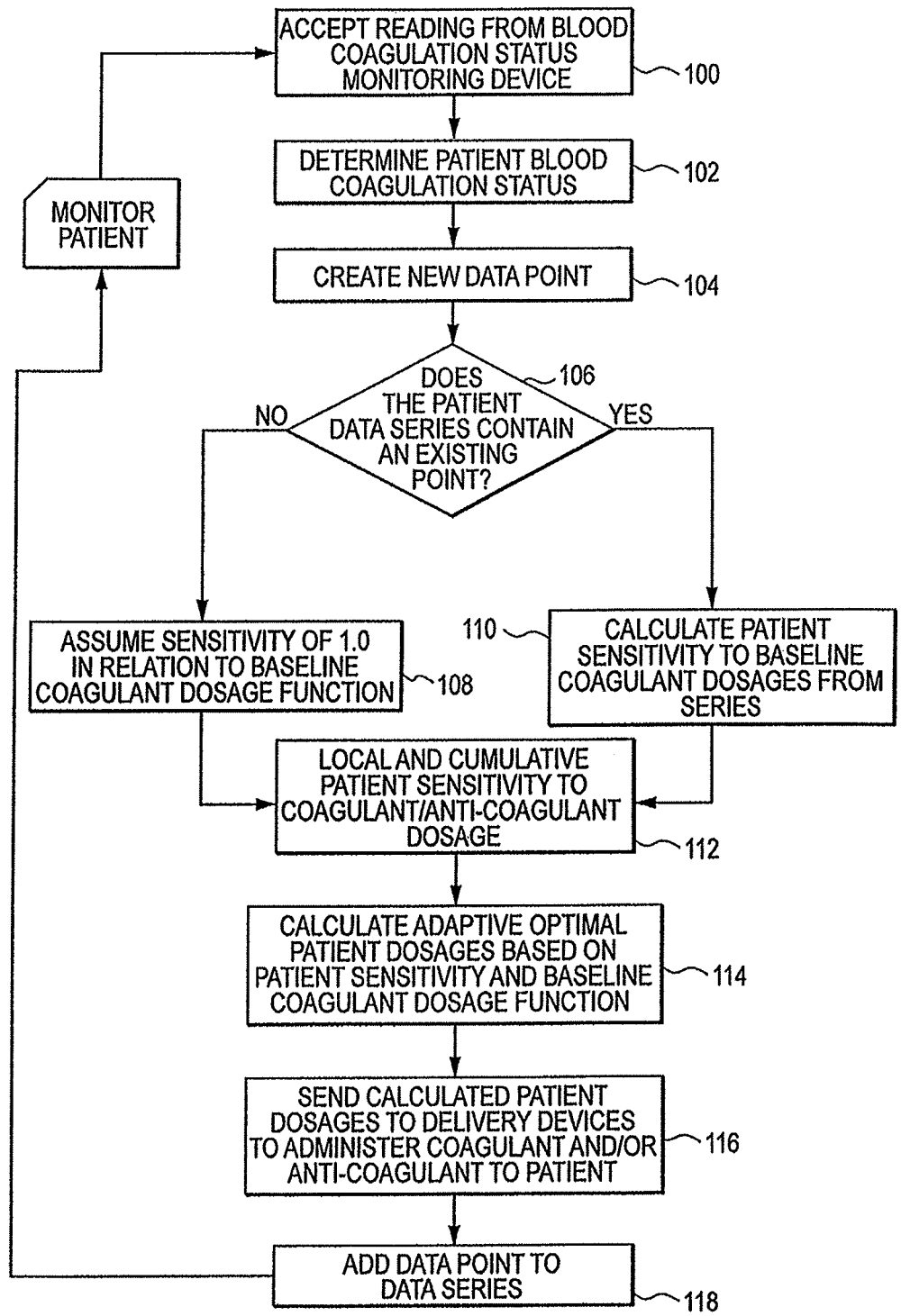
FIG. 4 is a flowchart illustrating another method of monitoring and stabilizing a physiological condition in accordance with the system of the present invention for an alternate embodiment.
Figure 5:
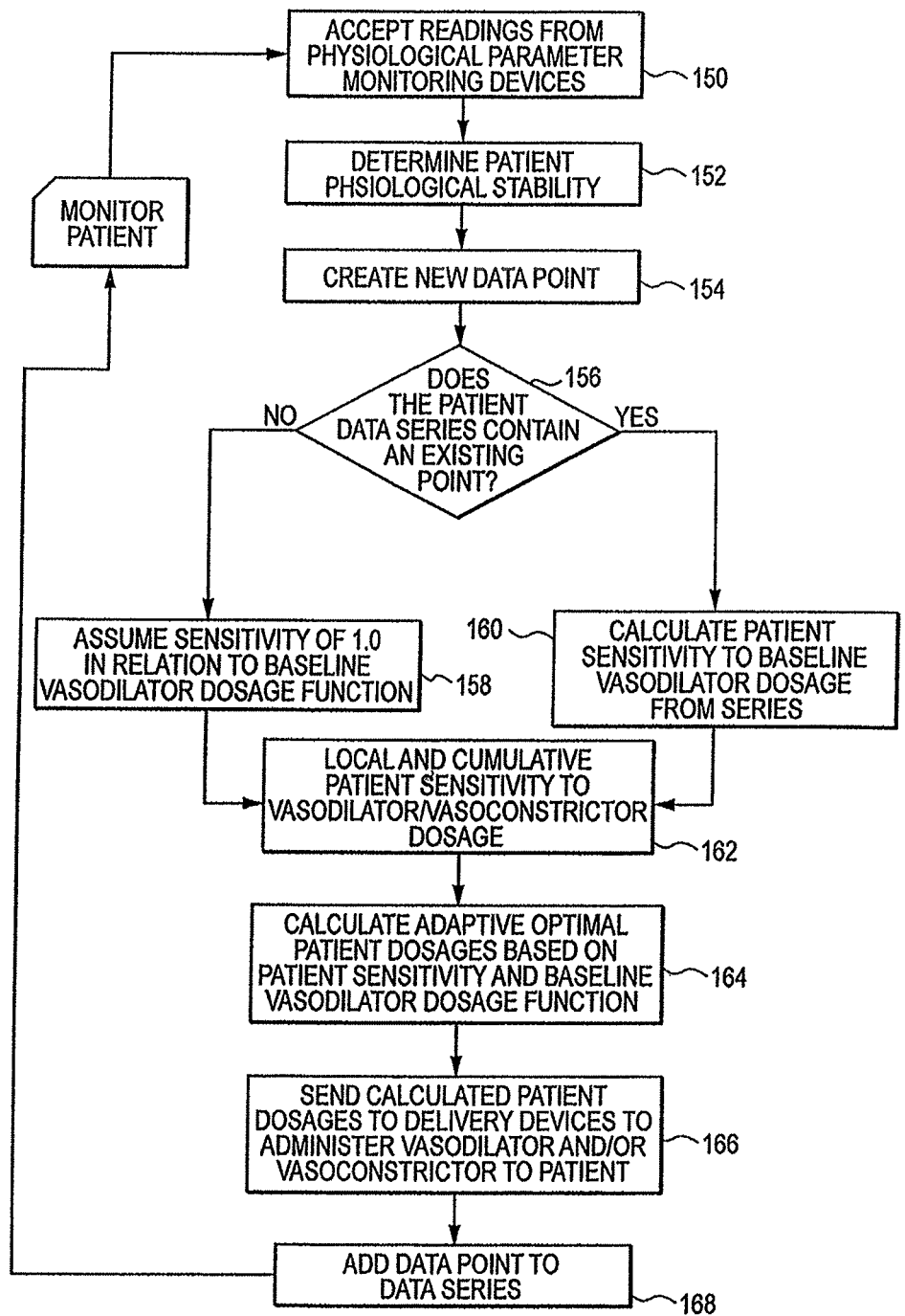
FIG. 5 is a flowchart illustrating a third method of monitoring and stabilizing a physiological condition in accordance with the system of the present invention.

FIGS. 3-5 depict examples of various methods used to monitor and control specific physiological conditions according to the present invention. As those skilled in the art will appreciate, various changes can be made to the methods, systems and physiological conditions and parameters being monitored without departing from the scope of the present invention. Thus, the examples present herein are not intended to limit, in any way, the scope of the present invention.

FIG. 3 depicts a method for monitoring and controlling a patient's blood glucose level including accepting a reading from a blood glucose monitoring device 80; determining the patient's blood glucose level 82; creating a new data point 84; determining if the patient data series contains an existing data point 86; calculating patient sensitivity to a baseline glucose dosage function if there are existing data points 90 or assuming a sensitivity of 1.0 in relation to the baseline glucose dosage function if there are not existing data points 88; determining local and cumulative patient sensitivity to glucose and/or insulin dosages 92; calculating adaptive optimal patient dosages based on the patient sensitivity and baseline glucose dosage function 94; sending the calculated patient dosages to the delivery devices to administer glucose and/or insulin to a patient 96; and adding a data point to the data series in order to continue to provide cumulative patient sensitivity information in order to calculate future dosages of glucose and/or insulin to be administered to the patient 98.

Referring now to FIG. 4, there is shown a method for monitoring and controlling a patient's blood coagulation status including accepting a reading from a blood coagulation status monitoring device 100; determining the patient's blood coagulation status 102; creating a new data point 104; determining if the patient data series contains an existing data point 106; calculating patient sensitivity to a baseline coagulant dosage function if there are existing data points 110 or assuming a sensitivity of 1.0 in relation to the baseline coagulant dosage function if there are not existing data points 108; determining local and cumulative patient sensitivity to coagulant and/or anti-coagulant dosages 112; calculating adaptive optimal patient dosages based on the patient sensitivity and baseline coagulant dosage function 114; sending the calculated patient dosages to the delivery devices to administer an anticoagulant and/or a coagulant to a patient 116; and adding a data point to the data series in order to continue to provide cumulative patient sensitivity information for calculating future dosages of the coagulant and/or the anti-coagulant to be administered to the patient 118. In this embodiment, the coagulant may include extrinsic and extrinsic clotting factors and clotting factor stimulants or like substances. The anticoagulant may include vitamin K, urokinase, streptokinase, heparin and other direct and indirect clotting factor inhibitors.

Referring now to FIG. 5, there is depicted a method for monitoring and controlling the stability of a patient in the intensive care unit of a hospital or a patient being treated in an emergency situation. This embodiment illustrates a method for concurrently monitoring at least two physiological parameters to provide a synthesized control signal to the delivery device 40 in order to stabilize the patient's condition. The method of this embodiment includes accepting a reading from at least two physiological parameter monitoring devices 150, including blood flow, blood pressure, heart rate, hemoglobin level, cardiac output, arterial oxygen concentration and any other physiological parameters that are affected by vasoconstriction and/or vasodilatation; determining the patient's overall physiological stability 152; creating a new data point 154; determining if the patient data series contains an existing data point 156; calculating patient sensitivity to a vasodilator dosage function if there are existing data points 160 or assuming a sensitivity of 1.0 in relation to the baseline vasodilator dosage function if there are not existing data points 158; determining local and cumulative patient sensitivity to a vasodilator dosage and/or a vasoconstrictor dosage 162; calculating adaptive optimal patient dosages based on the patient sensitivity and the baseline vasodilator dosage function 164; sending the calculated patient dosages to the delivery devices to administer the vasodilator and/or the vasoconstrictor to a patient 166; and adding a data point to the data series in order to continue to provide cumulative patient sensitivity information in order to calculate future dosages of the vasodilator and/or the vasoconstrictor to be administered to the patient 168. In this embodiment, the vasodilator is selected from the group including nitric oxide, L-arginine, alpha blockers, beta agonists, potassium channel openers, calcium channel blockers, angiotensin inhibitors and phosphodiesterase inhibitors. The vasoconstrictor is selected from the group including endothelin, endothelin like compounds, sympathomimetics and vasopressin like compounds.

The control logic of the controller 30 is derived by an algorithm and is comprised of two primary sets of equations.

In one embodiment, the algorithm based logic performs the following series of operations using blood glucose as an example. First, an optimal blood-glucose function, g(t), is derived. This function will govern the delivery device 40 target levels for all patients' blood-glucose measurements over time. The approach used is parameterized such that the optimal values for blood-glucose levels over time may be refined or changed without altering the logical framework. The rate of change in a patient's blood-glucose level should decline at a constant rate, so as not to shock the patient's system. In addition, the patient's blood-glucose level will decline more quickly when higher and more gradually when closer to the target level, allowing the patient to gently settle into a stability zone. This principle holds that acceleration, g"(t), should be a negative arbitrary constant (scalar quantity). The definition of the optimal blood-glucose function, g(t), can then be derived for the delivery device 40 by specifying either: a reference blood-glucose level and a time-to-target, or an acceleration constant, a, as well as boundary conditions, including the target blood-glucose level and the maximum blood-glucose level for which the delivery device 40 will regulate the patient.

Second, an optimal dose of insulin and/or glucose to be administered to a specific patient at any time is determined. This method is designed to regulate a specific patient's blood-glucose level according to the optimal blood-glucose function described above. The method considers a "baseline" dosage function, adapting to a patient's current metabolic state by refining a patient-specific forward-looking "sensitivity multiplier" (.mu.) with each additional blood-glucose measurement and/or dosage. The baseline dosage function can be explicitly defined via mathematical modeling as previously described. In an alternate embodiment, the baseline dosage function is calculated using patient specific data that characterizes the baseline dosage function, such as blood glucose level, insulin level and the like. In another alternate embodiment, the baseline dosage function is selected from a group of functions relating to patient attributes, such as previous insulin dosage, age, weight, medications, and clinical condition.

Third, an expected response function is defined explicitly. Alternately, the expected response function can be calculated from data that characterizes the expected result function, such as typical response of general populations of patients to medications, such as like glucose and/or insulin, under given conditions. The expected response function can also be a combination of the aforementioned options, where it can be explicitly defined via mathematical modeling while incorporating a reaction factor that is used to modify the expected response function based on detected events, the patient's condition and the like. Output of the expected response function for an interval of time is compared to the patient's demonstrated response or actual measured change in blood-glucose level over this same interval. The inverse of this ratio is then appended to the series of such ratios over all measurements for the current patient to establish a localized sensitivity to a medication for an interval of time.

Last, a cumulative patient-specific sensitivity multiplier, to be used in the next dosage (.mu..sub.n+1), is then calculated using a time-weighted average over the entire data series, in which localized sensitivity at each data point is weighted more heavily than the point preceding it. This patient-specific sensitivity multiplier is used in conjunction with the baseline dosage function to calculate subsequent patient-adapted dosages of the medications being administered. In this manner, the entire history of the patient's response to various dosage levels factors into each next dosage, with the patient's more recent demonstrated sensitivity being weighted more heavily.

In an alternate embodiment, the optimal dosage function is based on more than one physiological parameter. For example, as depicted in FIG. 5, in determining the optimal dose for the vasoconstrictor and/or the vasodilator, the baseline vasodilator function is based on determining a reference blood pressure, a reference heart rate, a reference hemoglobin level, arterial oxygen concentration and a reference cardiac output in addition to target times for all of these reference levels. Alternatively, the baseline vasodilator function can be based on determining acceleration constants with boundary conditions for the patient's blood pressure, heart rate, hemoglobin level arterial oxygen concentration and cardiac output, where the boundary conditions include target and maximum levels for each of these parameters.

The controller can be configured to store data relating to physiological parameter data (blood glucose levels, insulin levels, blood coagulation status, and the like), patient-adapted dosages and patient-specific sensitivities in order to observe and classify patterns in physiological behavior. The physiological behavior patterns can be matched with previously defined patterns based on physiological parameter data, patient-adapted dosages and patient-specific sensitivities.

In this embodiment, the series of data points are calculated based on the baseline vasodilator function, v(t). Because this embodiment is a multivariable system, model predictive control (MPC) is one effective method for controlling the vasodilator and vasoconstrictor delivery devices 42, 44. The model can be steady state or dynamic. Alternately, the system can also be based on equations that predict the affects of the vasodilators and vasoconstrictors on the patient's physiological parameters, empirical data collected in relation to a particular patient, or a combination thereof.

In an alternate embodiment, the model is an empirical, mathematical model including a set of coefficients, such as probability coefficients, applied to recent values of the parameter inputs (e.g., blood pressure, heart rate, hemoglobin level, arterial oxygen concentration and cardiac output) in order to predict future output values to be sent to the delivery devices 42, 44 for administering the vasodilator and/or the vasoconstrictor to the patient. These coefficients can be multiplied by a sensitivity factor, similar to the sensitivity multiplier previously discussed, by using a time-weighted average over the entire series, in which each data point is weighted more heavily than the points preceding it. In this manner, the entire history of patient's response to previous dosage levels is factored into each next dosage, with the patient's more recent demonstrated sensitivity being weighted more heavily.

Figure 6:
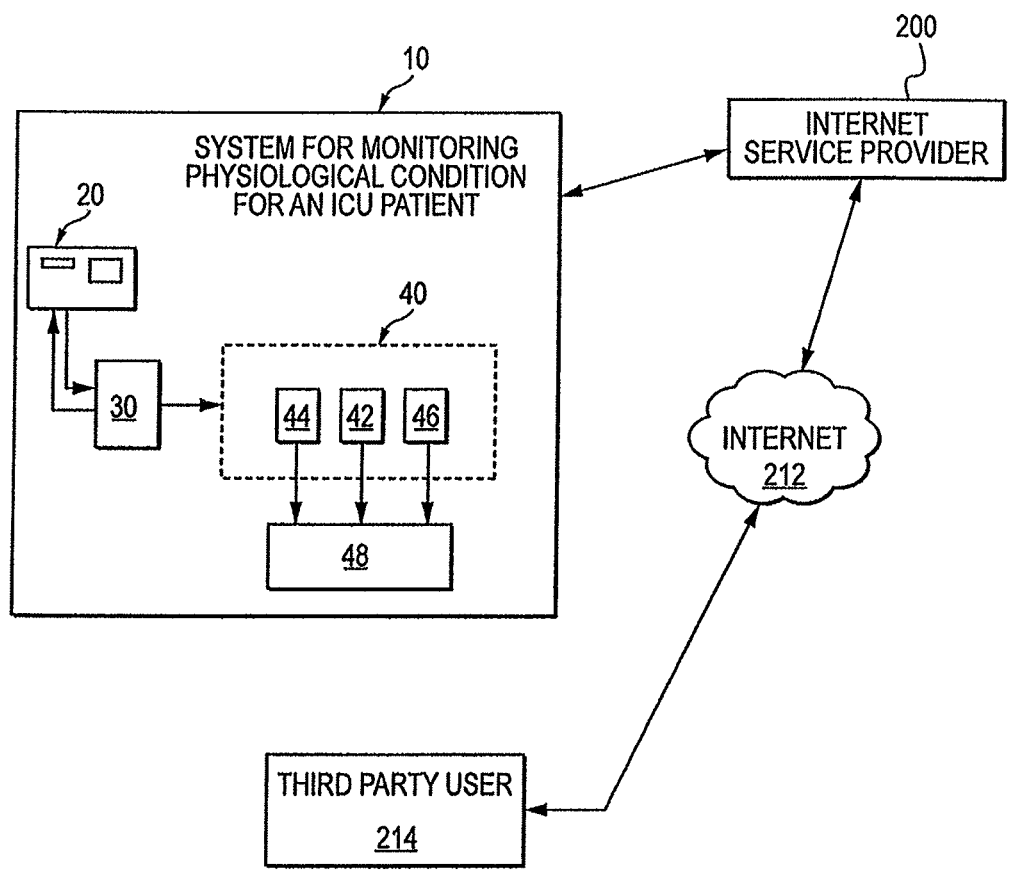
FIG. 6 is a block diagram illustrating exemplary components of the system of the present invention as it is incorporated into to a network system for remote access and control.

Referring now to FIG. 6, in an alternate embodiment in accordance with the present invention, system 10 may be integrated with a network 210 for remote monitoring, management and control of multiple delivery devices 40. The networked system 10 further allows for centralized data storage and archival of system information, patient information, measurement, calculation and administered dosage information. Additionally, the networked system 10 provides for information export and query capabilities that can be used for patient file management, health care facility management and medical research. Network 210 may be either locally contained or accessible via Internet 54 and optionally through an Internet service provider 200. Connection to network 210 may be wired or, alternatively, wireless and may incorporate control from a detached device (e.g., handheld, laptop, tablet, or other mobile device). In addition, system 10 may be accessible remotely by a third party user 214 via Internet 212 and Internet service provider 200.

Figure 7:
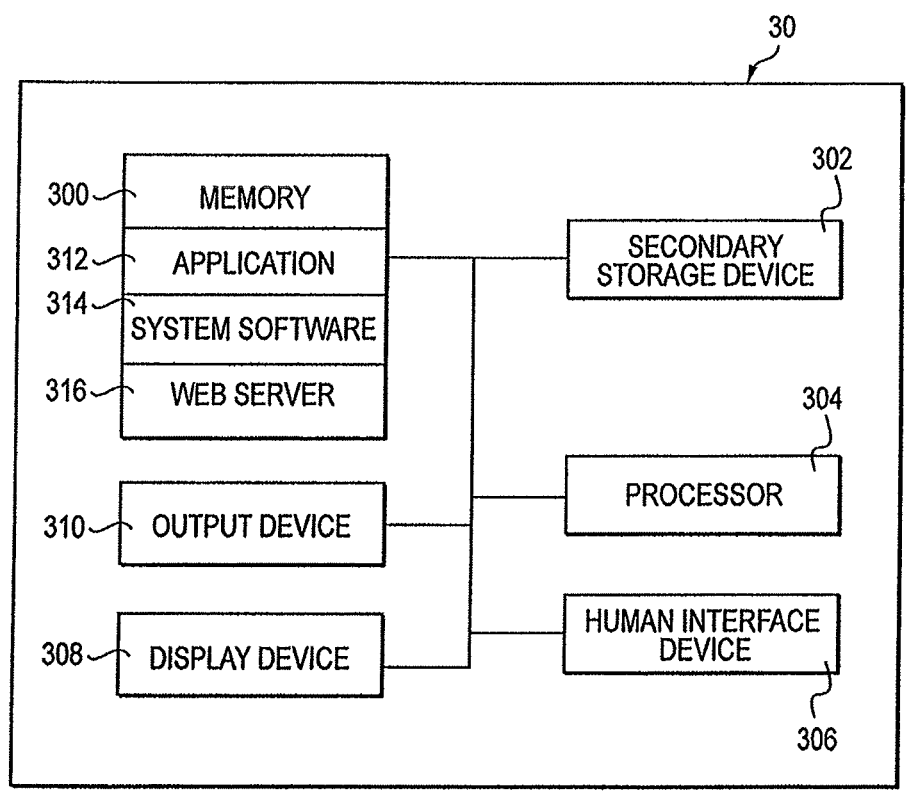
FIG. 7 is a block diagram of the exemplary components of an electronic controller used in the system of the present invention.

Referring now to FIG. 7, controller 30 illustrates typical components of a controller. Controller 30 typically includes a memory 300, a secondary storage device 304, a processor 304, an human interface device 306, a display device 308, and an output device 310. Memory 300 may include random access memory (RAM) or similar types of memory, and it may store one or more applications 312, including system software 314, and a web server 316, for execution by processor 304. Secondary storage device 302 may include a hard disk drive, floppy disk drive, CD-ROM drive, or other types of non-volatile data storage. The local cache that includes a patient's physiological condition data may be stored on secondary storage device 302. Processor 304 may execute system software 314 and other applications 312 stored in memory 300 or secondary storage 302, or received from Internet 212 or other network 210 (referring to FIG. 6). Processor 304 may execute system software 314 in order to provide the functions described in this specification including balanced, automated regulation of a physiological condition in ICU patients. Human interface device 306 may include any device for entering information into controller 30, such as a keyboard, mouse, cursor-control device, touch-screen, infrared, microphone, digital camera, video recorder, or any other instrument or device necessary to monitor physiological conditions and measure physiological parameters for ICU patients. Display device 308 may include any type of device for presenting visual information such as, for example, a computer monitor or flat-screen display. Output device 310 may include any type of device for presenting a hard copy of information, such as a printer, and other types of output devices include speakers or any device for providing information in audio form.

Web server 316 is used to provide access to patient data stored in memory 300 and on secondary storage devices 302 and display the data. Web server 316 allows users secure remote access to the system through which they can monitor and control status and operation of the treatment system and access patient data. Web server 316 can allow access to a user running a web browser. Examples of web browsers include the Netscape Navigator program and the Microsoft Internet Explorer program. Any web browser, co-browser, or other application capable of retrieving content from a network and displaying pages or screens may be used.

Examples of controllers 30 for interacting within the physiological monitoring and treatment system 10 include personal computers, laptop computers, notebook computers, palm top computers, network computers, Internet appliances, or any processor-controlled device capable of executing a web browser 316, system software 314 and any other type of application 312 stored in memory 300 or accessible via secondary storage device 302.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed:

1. A system for monitoring and controlling a physiological condition of a patient, comprising:

at least one physiological parameter monitor adapted to monitor at least one physiological parameter of a patient;

a control device operably connected to said at least one physiological parameter monitor, said control device having control logic for optimization of patient-specific sensitivity to dosage by monitoring, receiving and storing physiological parameter data generated from said physiological parameter monitor and translating said physiological parameter data into an output control signal containing information regarding administration of at least two counterbalancing medications based on said patient-specific sensitivity to dosage; and a multi-channeled delivery mechanism operably connected to said control device and capable of receiving said output control signal from said control device, said multi-channeled delivery mechanism being structured to infuse said at least two counterbalancing medications into the patient based on said patient-specific sensitivity to dosage information contained in said output control signal.

2. The system of claim 1 wherein said physiological parameter monitor measures blood glucose level.

3. The system of claim 2 wherein said at least two counterbalancing medications infused into the patient are glucose and insulin.

4. The system of claim 1 wherein said physiological parameter monitor measures blood coagulation status.

5. The system of claim 4 wherein said at least two counterbalancing medications are a coagulant and an anti-coagulant.

6. The system of claim 1 wherein said at least one physiological parameter monitor comprises a first physiological parameter monitor configured to monitor blood pressure, a second physiological parameter monitor configured to monitor heart rate, a third physiological parameter monitor configured to monitor hemoglobin level, and a fourth physiological parameter monitor configured to monitor cardiac output and a fifth physiological parameter monitor configured to monitor arterial oxygen concentration and a sixth physiological parameter monitor configured to monitor at least one circulating factor from the group consisting of vasoactive and inflammatory factors.

7. The system of claim 6 wherein said at least two counterbalancing medications are selected from the group consisting of a vasodilator and a vasoconstrictor.

8. The system of claim 1 wherein said control logic further comprises an algorithm for monitoring and controlling said at least one physiological parameter, said algorithm configured to determine baseline dosage functions for said at least two counterbalancing medications; determine expected response functions for said physiological parameter to said at least two counterbalancing medications; analyze the patient's demonstrated response to said at least two counterbalancing medications to derive said patient-specific sensitivity to said at least two counterbalancing medications; and use said patient-specific sensitivity in conjunction with said baseline dosage functions to calculate patient-adapted dosages of said at least two counterbalancing medications.

9. The system of claim 8 wherein at least one of said baseline dosage functions is explicitly defined.

10. The system of claim 8 wherein at least one of said baseline dosage functions is calculated using data that characterize said baseline dosage function.

11. The system of claim 8 wherein at least one of said baseline dosage functions is selected from a group of baseline dosage functions based on data relating to patient attributes.

12. The system of claim 8 wherein at least one of said expected response functions is explicitly defined.

13. The system of claim 8 wherein at least one of said expected result functions is calculated from data that characterize said expected result function.

14. The system of claim 8 wherein at least one of said expected result functions is configured to change over time in reaction to detected events and patient conditions.

15. The system of claim 8 wherein said algorithm observes and classifies patterns in physiological behavior based on known patterns in physiological behavior using factors selected from the group consisting of physiological parameter data, patient-adapted dosages of said at least two counterbalancing medications, and patient-specific sensitivity to said at least two counterbalancing medications.

16. The system of claim 15 wherein said algorithm observes and identifies patterns in physiological behavior to define new known patterns using factors selected from the group consisting of physiological parameter data, patient-adapted dosages of said at least two counterbalancing medications, and patient-specific sensitivity to said at least two counterbalancing medications.

17. The system of claim 16 wherein said control logic is configured to alter said algorithm in response to classifying at least one of said patterns in physiological behavior based on said known patterns.

18. The system of claim 8 wherein said patient-specific sensitivity to at least one of said at least two counterbalancing medications is further analyzed by calculating a cumulative patient-specific sensitivity to at least one of said at least two counterbalancing medications, said cumulative patient-specific sensitivity calculated by applying a weighted average to said localized patient-specific sensitivity over all known points in a series of patient data.

19. The system of claim 8 wherein said control logic monitors two or more physiological parameters in order to control the patient's overall physiological stability.

20. The system of claim 19 wherein said control logic includes an empirical, mathematical model for calculating probability coefficients based on a data series of said physiological parameters being monitored, said probability coefficients being used to predict future values in said data series.

21. The system of claim 20 wherein said control logic calculates said patient-adapted dosage by using predictive modeling in conjunction with patient-specific sensitivity data.

22. The system of claim 1 wherein said delivery mechanism comprises a plurality of infusion pumps configured to infuse a plurality of medications into the patient.

* * * * *